United States Patent
Tseng et al.

[11] Patent Number: 5,904,152
[45] Date of Patent: May 18, 1999

[54] DENTAL FLOSS

[75] Inventors: Mingchih M. Tseng, Hingham; Thomas Craig Masterman, Boston; Edward Hosung Park, Sharon; Michael F. Roberts, Quincy; Jean L. Spencer, Boston, all of Mass.

[73] Assignee: Gillette Canada Inc., Kirkland, Canada

[21] Appl. No.: 08/833,643

[22] Filed: Apr. 8, 1997

Related U.S. Application Data

[63] Continuation of application No. 08/467,814, Jun. 6, 1995, abandoned.

[51] Int. Cl.⁶ .................................................. A61C 15/00
[52] U.S. Cl. .................................... 132/321; 132/323
[58] Field of Search ........................... 132/321, 323–329; 428/370, 373, 374; 433/15, 11, 18

[56] References Cited

U.S. PATENT DOCUMENTS

| | | |
|---|---|---|
| 802,711 | 10/1905 | Schrader . |
| 2,381,142 | 4/1945 | Stonehill . |
| 2,667,443 | 1/1954 | Ashton . |
| 2,700,636 | 1/1955 | Ashton . |
| 2,748,781 | 6/1956 | Collat . |
| 3,120,670 | 2/1964 | Amodeo . |
| 3,412,192 | 11/1968 | Clapson . |
| 3,423,923 | 1/1969 | Hume . |
| 3,492,131 | 1/1970 | Schlatter . |
| 3,531,368 | 9/1970 | Okamoto et al. . |
| 3,558,419 | 1/1971 | Okazaki et al. . |
| 3,594,266 | 7/1971 | Okazaki et al. . |
| 3,615,671 | 10/1971 | Shoaf et al. . |
| 3,616,149 | 10/1971 | Wincklhofer et al. . |
| 3,616,167 | 10/1971 | Gosden . |
| 3,642,491 | 2/1972 | Schlatter . |
| 3,645,819 | 2/1972 | Fujii et al. . |
| 3,679,541 | 7/1972 | Davis et al. . |
| 3,692,423 | 9/1972 | Okamoto et al. ........................ 425/131 |
| 3,699,979 | 10/1972 | Muhler et al. . |
| 3,771,536 | 11/1973 | Dragan . |
| 3,789,858 | 2/1974 | Pesce . |
| 3,800,046 | 3/1974 | Schlatter . |
| 3,814,561 | 6/1974 | Matsui et al. ........................... 425/131 |
| 3,830,246 | 8/1974 | Gillings . |
| 3,837,351 | 9/1974 | Thornton ................................. 132/321 |
| 3,838,702 | 10/1974 | Standish et al. . |
| 3,896,824 | 7/1975 | Thornton . |
| 3,897,795 | 8/1975 | Engel . |
| 3,943,949 | 3/1976 | Ashton et al. . |
| 3,957,067 | 5/1976 | Ferraro et al. . |
| 3,968,307 | 7/1976 | Matsui et al. . |
| 3,978,267 | 8/1976 | Selwood . |
| 3,998,988 | 12/1976 | Shimomai et al. . |
| 4,008,727 | 2/1977 | Thornton . |
| 4,019,311 | 4/1977 | Schippers . |
| 4,029,113 | 6/1977 | Guyton . |
| 4,033,365 | 7/1977 | Klepak et al. . |
| 4,071,615 | 1/1978 | Barth . |
| 4,122,658 | 10/1978 | Morioka et al. . |
| 4,142,538 | 3/1979 | Thornton . |

(List continued on next page.)

FOREIGN PATENT DOCUMENTS

| | | |
|---|---|---|
| 118695 | 4/1943 | Australia . |
| 080440A1 | 6/1983 | European Pat. Off. . |
| 335466A2 | 10/1989 | European Pat. Off. . |
| 23 40 208 A1 | 2/1975 | Germany . |
| 2216803 | 10/1989 | United Kingdom . |

OTHER PUBLICATIONS

Bauermeister, "Method of Preparing Dental Remedies", Letter Patent No. 660,943, Oct. 30, 1990.

Clark, "Improvement in Tooth–Picks", Letter Patents No. 174,619, Mar. 14, 1876.

*Primary Examiner*—Gene Mancene
*Assistant Examiner*—Pedro Philogene
*Attorney, Agent, or Firm*—Fish & Richardson P.C.

[57] ABSTRACT

Improved dental flosses are provided, including multicomponent coextruded filaments and/or filaments having a multilobal cross-section. Some preferred flosses of the invention are capable of bulking.

33 Claims, 4 Drawing Sheets

U.S. PATENT DOCUMENTS

| | | |
|---|---|---|
| 4,275,117 | 6/1981 | Crandall . |
| 4,291,017 | 9/1981 | Beierle et al. . |
| 4,350,006 | 9/1982 | Okamoto et al. . |
| 4,381,274 | 4/1983 | Kessler et al. .......................... 264/147 |
| 4,414,990 | 11/1983 | Yost . |
| 4,424,258 | 1/1984 | Bach ...................................... 428/370 |
| 4,447,489 | 5/1984 | Linhart et al. . |
| 4,548,219 | 10/1985 | Newman et al. . |
| 4,584,240 | 4/1986 | Herbert et al. .......................... 428/373 |
| 4,627,975 | 12/1986 | Lynch . |
| 4,638,823 | 1/1987 | Newman et al. . |
| 4,817,643 | 4/1989 | Olson . |
| 4,861,633 | 8/1989 | Abe . |
| 4,867,679 | 9/1989 | Rackley .................................... 433/15 |
| 4,911,927 | 3/1990 | Hill et al. . |
| 4,952,392 | 8/1990 | Thame . |
| 4,974,615 | 12/1990 | Doundoulakis . |
| 4,986,288 | 1/1991 | Kent et al. . |
| 4,996,056 | 2/1991 | Blass . |
| 4,998,978 | 3/1991 | Varum . |
| 5,033,488 | 7/1991 | Curtis et al. . |
| 5,063,948 | 11/1991 | Lloyd . |
| 5,166,309 | 11/1992 | Maj et al. . |
| 5,213,891 | 5/1993 | Maj et al. . |
| 5,284,169 | 2/1994 | Gilligan et al. ......................... 132/321 |
| 5,413,127 | 5/1995 | Hill . |
| 5,433,226 | 7/1995 | Burch . |
| 5,439,741 | 8/1995 | Gibbon et al. . |
| 5,479,952 | 1/1996 | Zachariades et al. . |
| 5,518,012 | 5/1996 | Dolan et al. ............................ 132/321 |

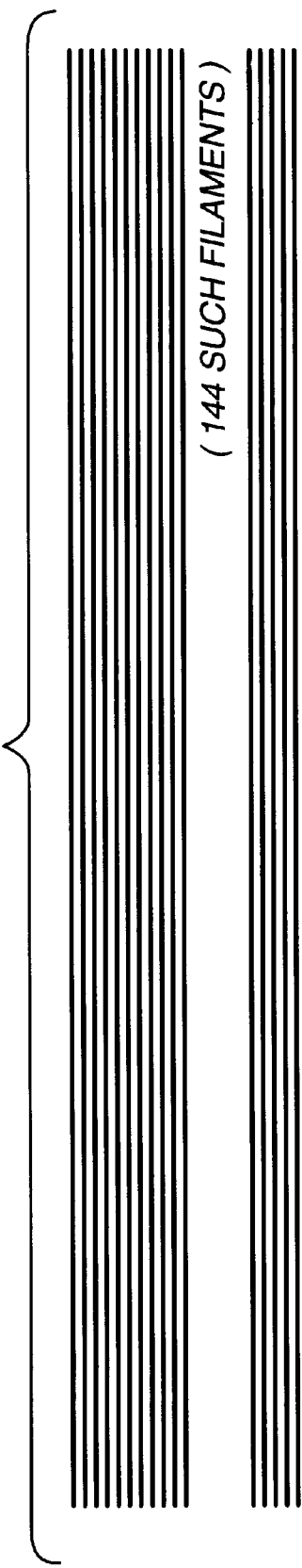
FIG. 1 (144 SUCH FILAMENTS)
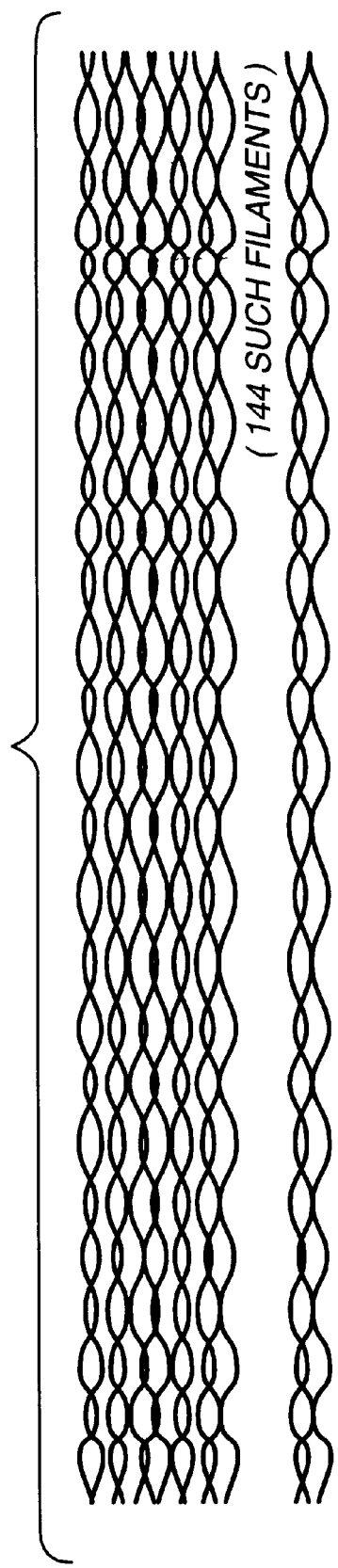
FIG. 1a (144 SUCH FILAMENTS)

  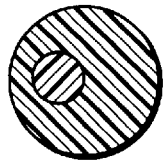  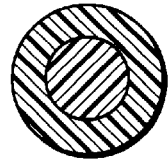
FIG. 3        FIG. 3a        FIG. 3b
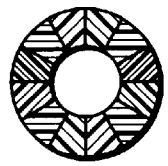        
FIG. 3c        FIG. 3d
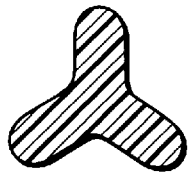      
FIG. 4     FIG. 4a     FIG. 4b 13.6 μm

DENTAL FLOSS

This is a continuation of application Ser. No. 08/467,814, filed on Jun. 6, 1995, now abandoned.

BACKGROUND OF THE INVENTION

Tooth decay and dental disease can be caused by bacterial action resulting from the formation of plaque about the teeth and/or the entrapment of food particles in interstices between the teeth. Removal of plaque and entrapped food particles reduces the incidence of caries, gingivitis, and mouth odors as well as generally improving oral hygiene. Conventional brushing has been found to be inadequate for removing all entrapped food particles and plaque. To supplement brushing dental flosses and tapes have been recommended.

Dental flosses including a thickened "brush" portion have been developed. These flosses may also include a thin "floss" portion and a threader. The brush portion, when drawn between tooth surfaces, provides good cleaning action which removes materials left by a standard thin floss used alone.

To form a brush floss, it is necessary to provide bulked filaments in a strand of floss, i.e., filaments which are separated and have a somewhat sinuous, random orientation.

Dental flosses, both in brush and thin floss form, often include additives such as flavors or colors. These flavors have been conventionally applied by coating the additive onto the surface of the floss.

SUMMARY OF THE INVENTION

The present invention features improved dental flosses and filaments for use in manufacturing dental flosses. Preferably, the filaments are multicomponent coextruded filaments. By "multicomponent", we mean that the filaments have two or more components; by "coextruded", we mean that at least two of the components are present in the form of substantially separate phases having a distinct interface between them, rather than being intermixed. The filaments are preferably formed by processes which are referred to in the art as "coextrusion", but the term "multicomponent coextruded" as used herein, encompasses filaments having the structure described above which are manufactured by other processes.

In one aspect of the invention, the improved flosses of the invention include filaments that are capable of being "bulked" to form a brush floss.

The filaments may include polymers that have been partially or fully oriented, i.e., the molecules of the polymer have been extended from their normal position, during manufacture. Orientation is preferably obtained by pretensioning the filaments during the manufacturing process. When tension is released, e.g., by unwinding the floss from a spool, the filaments relax, causing the floss to bulk. These flosses are referred to herein as "self-bulking flosses", as they will bulk when tension is released without any other bulking step.

Alternatively, the filament may include polymers that are not oriented (or not oriented to any appreciable degree) during manufacture. Flosses containing these filaments, although they can be bulked using conventional methods, e.g., steam or hot air bulking, if desired, are preferably bulked simply by applying tension to the floss, causing orientation of the polymers, and then releasing the tension. These flosses can be bulked by a user of the floss immediately prior to use, or even while the floss is between the user's teeth, if desired. These flosses are referred to herein as "tension-induced bulking flosses".

Advantageously, both the "self bulking" and "tension-induced bulking" flosses can be bulked simply by applying tension to the floss. Bulking is believed to result from a combination of the differences in the relaxation rates of the various components of each multicomponent filaments the degree of adhesion at the interface between the components, and the geometry of the relative cross-sections of the components of each filament. Thus, these flosses can be easily manufactured without cumbersome additional manufacturing steps (e.g., polymer coating, selective solvent removal, steam or hot air treatment).

In preferred embodiments, the floss is twisted and coated either before bulking (in the case of tension induced bulking floss) or after bulking (in the case of self bulking floss). Some preferred flosses include both bulked and non-bulked portions, achieved by applying tension selectively to predetermined portions of the floss. Other preferred flosses include one or more additives incorporated into one or more of the components, e.g., a color which appears, or a flavor, scent or active ingredient which is released, upon bulking.

According to another aspect of the invention, improved dental flosses are formed of filaments that include two or more components selected to provide desired properties to the floss. For example, the filaments may include an inner core selected to provide strength to the floss, and an outer layer selected to provide a desired surface property, e.g., slipperiness, softness, or abrasiveness. Flosses according to this embodiment of the invention may or may not be capable of bulking, depending upon the combination of components selected.

A further aspect of the invention features improved dental flosses that include filaments in which one or more of the filament components includes an additive, e.g., a color, fragrance, flavor or active ingredient, which is releasable from the floss. Some preferred flosses are capable of bulking. Some preferred flosses include a combination of components selected to give the floss desired properties other than bulking e.g., surface properties such as slipperiness combined with good tensile strength. The additive-containing components may be water-soluble, to allow the additive to leach from the floss during use, or the floss may release the additive upon bulking. The additive may be provided as supplied, in microencapsulated form, or adsorbed or absorbed onto another additive, e.g., a particulate filler. The additive can also be provided on charged microspheres, as described in U.S. Pat. No. 5,300,290, the disclosure of which is incorporated herein by reference.

Advantageously, additives can be incorporated into the flosses of the invention during manufacture of the filaments, rather than applying the additives later during separate coating steps. This not only reduces the number of processing steps, but also reduces the amount of additive needed.

In yet another aspect, the invention features improved flosses that include filaments which have a multilobal cross-section These flosses may include single component or multicomponent filaments, and, in the latter case, may or may not be capable of bulking. The multilobal cross-section may improve the comfort and cleaning properties of the floss.

The invention further features methods of making the improved flosses. A preferred method includes (a) coextruding two or more polymers through a multicomponent die to form a plurality of multicomponent filaments; and (b) treating the filaments to form a fiber adapted for use as a dental floss.

Additionally, the invention features methods of flossing the teeth of a mammal, e.g., a human, by inserting between two teeth of the mammal a length of a dental floss of the invention.

The term "dental floss", as used herein, is defined to include dental flosses, dental tapes, and similar articles.

Other features and advantages of the invention will be apparent from the drawings, the following Detailed Description, and the claims.

BRIEF DESCRIPTION OF THE DRAWINGS

FIG. 1 is a schematic, highly enlarged, side view of a length of dental floss prior to bulking. FIG. 1a is a schematic, highly enlarged, side view of the dental floss of FIG. 1 after bulking.

FIGS. 3–3d are cross-sectional views, taken radially, of multicomponent coextruded filaments having various cross-sections.

FIG. 4 is a cross-sectional view, taken radially, of a trilobal single component filament according to one embodiment of the invention. FIG. 4a is a cross-sectional view, taken radially, of a trilobal multicomponent filament having a sheath/core cross-section; FIG. 4b is a cross-sectional view, taken radially, of a trilobal multicomponent filament having a tipped cross-section.

DESCRIPTION OF THE PREFERRED EMBODIMENTS

Bulking Flosses

Figure 2:
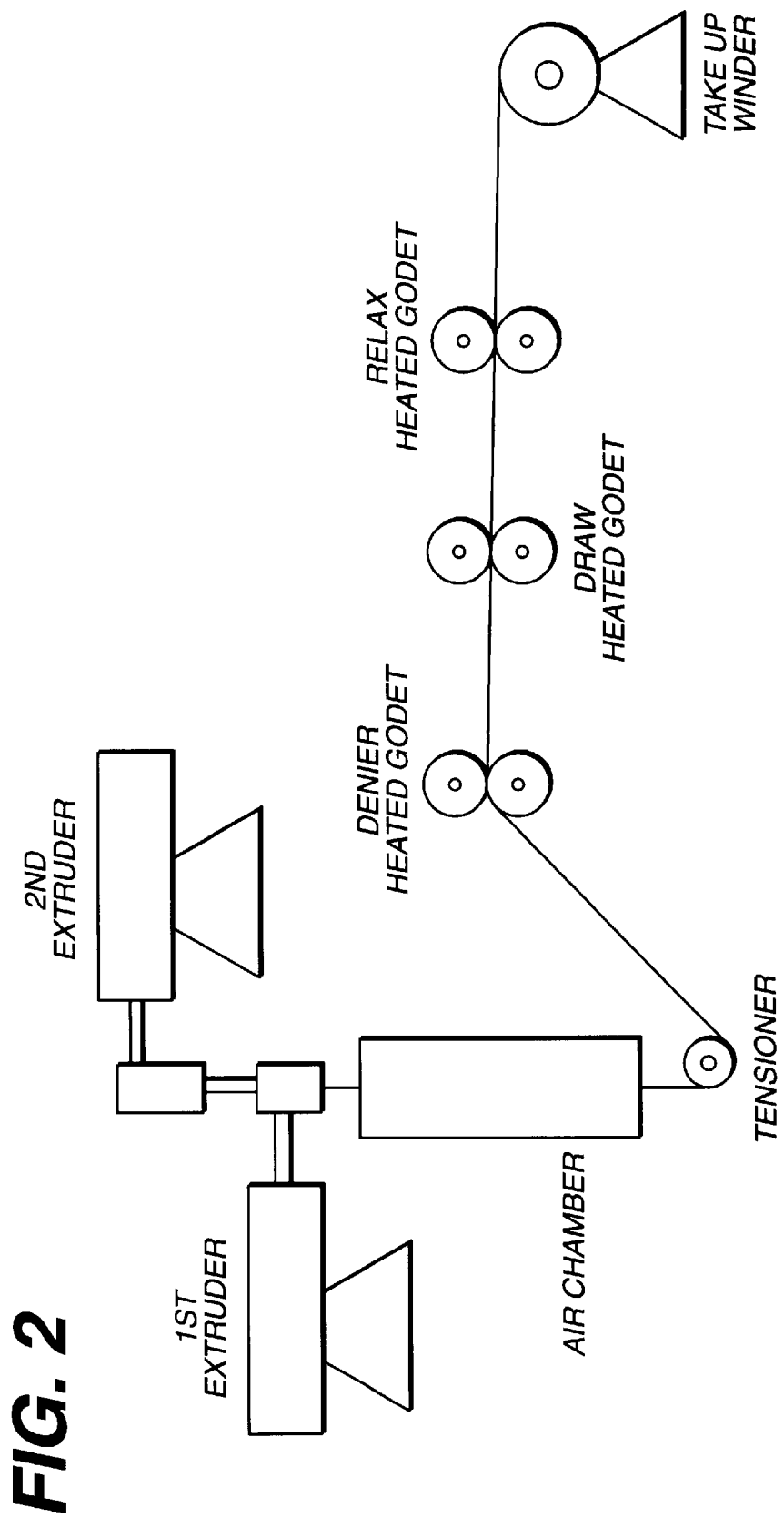
FIG. 2 is a schematic view of a production line for manufacturing a self-bulking brush dental floss according to one embodiment of the invention.

Referring to FIGS. 1 and 1a, a length of dental floss is shown before and after bulking. Prior to bulking, the filaments which comprise the floss are arranged close together to form a fiber and are substantially parallel to each other in the axial direction (FIG. 1).

After bulking, as shown in FIG. 1a, the dental floss is in the form of a brush, i.e., the filaments are relatively widely spaced and are no longer substantially axially parallel, but instead are somewhat sinuous and randomly oriented. Preferably, the brush floss has, in its relaxed state, a diameter that is at least 300 to 550 percent of the original diameter of the fiber prior to bulking, and a denier of from about 500 to 700. Preferred brush flosses have sufficient strength to resist fraying and breaking during use, typically a breaking strength of at least 5 N, preferably at least 10 N, more preferably about 25 N.

Under tension, during use, the brush stretches to become a thread, suitable for easy insertion between the teeth and for upward and downward scraping motion along the opposed tooth surfaces When not under tension, the brush is yarn-like, suitable for cleaning between the teeth in a brushing action, pulling the brush floss back and forward across tooth and gingival surfaces.

The floss is formed of a fiber comprising a plurality of multicomponent filaments formed of two or more polymeric components. The components are selected to exhibit differing rates of relaxation as a result of their viscoelasticities and/or crystalline structure, and/or to have relative cross-sections, and/or to have a degree of adhesion at their interface, which will result in bulking upon orientation and subsequent relaxation of the filaments.

A difference in relaxation rate can be achieved by utilizing distinct polymers, e.g., nylon and polyester, or different grades of the same polymers i.e., grades having different Melt Flow Indices (MFIs), relative viscosities (RVs) or molecular weights The polymers preferably have different viscoelasticities, and/or different crystalline structure, e.g., a different ratio of crystalline to amorphous material. It is noted that even if one or more of the components (although not all of the components of the filament) is stretched to a point exceeding the elastic limit of the component, such that for all practical purposes relaxation of these components does not occur, the filament will still generally be capable of bulking.

A difference in cross-section can be achieved by, e.g., arranging the components so that their cross-sections are assymmetric, or so that they occupy unequal percentages of the volume of the filament. Suitable cross-sections for the filaments include side-by-side (FIG. 3), sheath/core eccentric (FIG. 3a), sheath/core (FIG. 3b), hollow pie (FIG. 3c) and pie (FIG. 3d)

A degree of adhesion which will result in bulking can be readily determined empirically. Generally, materials having lesser adhesion to each other will have a greater tendency to cause bulking when combined in a filament. If desired, agents can be added to modify the adhesion of the materials, decreasing the adhesion of compatible components or increasing the adhesion of otherwise incompatible components. These agents are well known in the plastics art.

Suitable material combinations include but are not limited to nylon and polyester; high MFI polypropylene (e.g., having an MFI of from 20 to 50) and low MFI polypropylene (ego., 5 to 20); high RV nylon (e.g., having an RV of from 3 to 5) and low RV nylon (e.g., 1 to 3); polyester and polypropylene; and nylon and polypropylene. Preferably, the two components are provided in a volumetric ratio of from about 5:95 to 95:5.

Methods of forming preferred self-bulking and tension-induced bulking brush flosses will now be described.

Self-Bulking Floss

A method for forming a preferred self-bulking dental floss is shown schematically in FIG. 2. Firsts two or more polymers are coextruded through a two component extrusion die to form a bicomponent filaments the physical properties and/or the relative cross-sections of the polymers being selected, as described above, to enable the floss to be bulked.

Preferably, the extrusion die includes a spinneret, as is known in the filament forming art, through which a plurality of these bicomponent filaments are extruded at once. Preferred flosses contain from 72 to 288 filaments and have a total denier of from about 500–3000. The filaments exiting the spinneret are gathered to form a fiber, which then passes through a cooling chamber, preferably at 0 to 30° C., and is placed under light tension as it travels between two drawing godets which are rotating at different speeds. The tension applied to the fiber is expressed as the "drawdown ratio", which is the speed differential between the two drawing godets. Preferred drawdown ratios are from about 1.0 to 5.0, more preferably about 1.5 to 4.0. The fiber then passes through a relaxing godet and is collected on a take-up winder. As soon as tension is removed from the fiber, the filaments of the fiber separate or "bulk", forming a brush.

The bulked fiber can then be further treated to form a finished brush floss. For example, preferred flosses are twisted, preferably about 1 to 1.5 twists per inch, and coated with a bonding solution. Twisting and coating reduces excessive filament separation and improves fray resistance. Twisting processes are well known, e.g., using standard ring twisting equipment. Coating may be accomplished in any suitable manner, e.g., by dip coating, i.e., imbibing the filament in a bath of the coating, removing the excess coating as the filament exits the bath, and drying the filament to remove solvent in an air stream. The drying rate may be accelerated by heating the air stream e.g., to 60° C. Suitable coating solutions include a coating of 80/20 GENTAL 101 nylon polymer (General Plastics, Bloomfield, N.J.) in ethanol, SPENLITE L89 or SPENKEL M21 polyurethane coating (Reichold Chemicals, Research Triangle Park, N.C.). The coating should be flexible enough not to inhibit bulking but heavy enough to bond the filaments adequately to prevent excessive fraying.

Tension Induced Bulking Floss

Tension induced bulking flosses are manufactured in a manner similar to that described above except that tension is not applied to the fiber at any time (other than incidental minor amounts of tension resulting from movement of the fiber through the processing equipment). Thus, the draw-down ratio is approximately 1.0, if equipment including the drawing godets is used (these godets are not necessary if no tension is to be applied, but can be left in place if it is desired to use the same production line to manufacture both self-bulking and tension-induced bulking flosses).

Ideally, for tension induced bulking flosses the fiber has, prior to bulking, a denier of approximately 1750–2800, so that when it is pulled to its natural draw limit range of about 3 to 4 it has a final denier of 500–700.

Specialty Bicomponent Filaments

In another embodiment of the invention, the filaments used to form the dental floss include two or more components, each of which contributes a desired property to the filament. These filaments may or may not impart bulking capability to the floss, depending upon the factors discussed above (relative relaxation rates, adhesion, cross-sectional geometry).

These filaments may be manufactured using the same process described above, preferably with tension applied during manufactures as described above for the self-bulking flosses. (Depending upon the components selected and cross-sectional geometry, the applied tension may or may not cause bulking; however, it is generally preferred to apply tension in any case, as this has been found to improve the tensile strength of the filaments.)

Some preferred filaments include an outer sheath which is soft, slippery, or abrasive, to improve the ease of insertion, comfort and cleaning capability, respectively, of the floss, and an inner core that provides other desired physical properties such as strength and resiliency and/or serves as a carrier for additives, such as flavors, scents and medicaments.

Where the outer layer is intended to provide softness, for ease of insertion, preferred polymers include TPEs (thermoplastic elastomers), e.g., polyether block amides such as those available under the tradename PEBAX from ELF Atochem, polyester elastomers such as those available under the tradename HYTREL from DUPONT, and styrene butadiene block copolymers such as those available under the tradename KRATON from Shell; EVA (ethylene vinyl acetate); ethylene-propylene copolymers; low MFI polypropylene, and mixtures thereof.

Where the outer layer is intended to provide slipperiness, for comfort during use, preferred polymers include polyethylene, melt extrudable fluoropolymers (e.g. polyvinylidene fluoride (PVDF), and fluorinated ethylene propylene copolymers), polymers containing polytetrafluoroethylene (PTFE) particles and/or silicone oil, melt extrudable lubricating polymers (e.g., polyoxyethylene such as is commercially available from Union Carbide under the tradename Polyox®, or triblock copolymers of polyethylene oxide and polypropylene oxide such as those available from BASF under the tradename Pluronic®), and melt extrudable lubricous polymer alloys (eg., Lubriloy® polymers available from LNP engineering plastics).

If the outer layer is to include an abrasive, for improved cleaning, preferred abrasive/polymer combinations include nylon containing particles of kaolin, calcium carbonate, zinc oxide, silica, PTFE, or blends of these particles which are compatible. If desired, one or more additives may be absorbed or adsorbed on the surface of the abrasive particles, e.g., by drum drying, spray drying, fluidized bed processing, or other suitable methods as is known in the art.

In all of the above cases, one of the polymers is preferably a reinforcing polymers e.g., nylon, polyester or polypropylene, to impart tensile strength and/or rigidity to the floss.

In one embodiment, one of the polymers may be selected to have a suitable melt temperature and other properties to enable the filaments to bond to each other to form the finished floss without the coating and twisting procedure described above. A suitable multicomponent fiber for use in this embodiment is described in Example 4, sample 1. The filaments are bonded by softening and flattening the fiber on a heated draw roll as it is being passed by the godets.

The sheath and core may have any suitable cross-section, preferably a symmetric sheath/core cross-section (FIG. 3b) or an eccentric sheath/core cross-section (FIG. 3a). The filament may also have a hollow pie cross-section (FIG. 3c), and, if desired, the hollow core may be filled with an additive, e.g., a flavors color or active ingredient.

Specialty bicomponent flosses can also be formulated to include one or more additives, e.g., a colors fragrances or active ingredient, in one or both of the components.

For example, the outer layer may be polyester, nylon or other thermoplastic, and the inner core may be a different thermoplastic (or different grade of the same thermoplastic) which contains an additive such as chlorhexidine (or a salt thereof), sodium fluorides flavor (e.g. Polyiff®, International Flavors and Fragrances), fragrance, tooth desensitizer, tooth whitener or other additives suitable for use in dental flosses. The thermoplastic to be used for the inner core will be determined by the additive used, as would be readily appreciated by one skilled in the art. Suitable polymers include nylon, polyester, polypropylene, ethylene vinyl acetate (EVA), polyvinyl alcohol, polyethylene and alike. The inner or outer polymer may be water soluble to allow the additive to leach out of the polymer.

Alternatively, the polymers may be selected to render the floss capable of bulking, and the additive can be released upon bulking. Release upon bulking can occur due to various mechanisms, or combinations of mechanisms. For example, the additive can be provided in encapsulated form, and the shearing action of bulking can rupture the capsules, or the portion of the additive present at the interface of the components can be exposed by separation of the components at the interface during bulking. A preferred material for the additive-containing component in this embodiment is polypropylene as its low extrusion temperature minimizes degradation of temperature-sensitive additives. The additive may be a color which is incorporated in a manner so that the color is only visible either before or after bulking, i.e. so that the floss changes color to indicate bulking. This can occur by various mechanisms, e.g., by the color being diluted by the expansion of the fiber during bulking, so that the floss changes from a color to white, by selecting the cross-section so that bulking exposes a component of a different color, or by one of the components being a polymer, such as ABS, which changes color when tension is applied to it.

The additive, if desired, can be incorporated in encapsulated form. Encapsulation may be used for thermal protection or moisture protection of the additive, and may be accomplished by any number of conventional techniques such as spray drying, drum drying or solvent evaporation. The additive can also be provided on a charged microsphere, as described in U.S. Pat. No. 5,300,290.

Suitable cross-sections include sheath/core, sheath/core eccentric, side-by-side, pie and hollow pie (see FIGS. 3–3d).

Multilobal Filaments

Other preferred flosses include a plurality of filaments having a multilobal cross-section, as shown in FIG. 4. Preferred filaments include from 3 to 8 lobes; one suitable filament has 3 lobes. The filaments are preferably formed by extrusion through a die having the appropriate multilobal cross-section.

These filaments may be multicomponent or single component, and, if the former, may have a sheath/core (FIGS. 4a), tipped (FIG. 4b), or other suitable cross-section. Suitable polymers for use in forming multilobal filaments include but are not limited to polyester, polypropylene and nylon. In multicomponent filaments, if desired the polymers may be selected, as described above, to render the floss capable of bulking Suitable methods of forming flosses using these multilobal filaments include any conventional floss manufacturing methods. The twisting and coating methods described above are preferred.

The following examples are intended to be illustrative and not of limiting effects.

EXAMPLES

Equipment Set-Up

The following equipment set-up and manufacturing procedure, shown schematically in FIG. 2, was used in all examples.

Two 1.5 inch diameter extruders were connected to a two component extrusion die. The two extruders included 30/1 L/D ratio general purpose screws. The two component extrusion included a metering plate, a distributing plate, etched plates, and a spinneret. After being coextruded through the extrusion die, the extrudate was processed with a downstream filament spinning set-up to produce filaments. The downstream set-up included a cooling chamber, finish applicator, tensioner, drawing godets, relaxing godet, and winder. The extrudate was cooled at the cooling chamber, stretched and relaxed by drawing and relaxing godets, and collected on the take-up winder.

Example 1

Manufacturing Dental Floss from Filaments Self-Bulking Floss

A fiber containing 144 bicomponent filaments of 70/30 nylon 6/PET (side-by-side cross-section) drawn using a drawdown ratio of 3.28, using the equipment and procedure described above, was converted to floss in the following manner.

The fiber was first twisted to reduce filament separation during flossing and to add fray resistance. Twisting was carried out using standard ring twisting equipment, at a twist level of 1.5 twists per inch once twisted, the filament was dip coated in a coating of 80/20 GENTAL 101 nylon polymer in ethanol. Removal of the solvent after dip coating was accelerated by heating the air stream to 60° C.

Tension-Bulked Floss

A fiber containing 144 bicomponent filaments, side-by-side cross-section, drawdown ratio of 1.0, 80/20 nylon 6/PET was used. A blue dye was incorporated into the nylon resin, and the PET was white (pigmented with $TiCO_2$).

To convert the fiber to a floss, the fiber was twisted to between 1 and 1.5 twists per inch, and subsequently dip-coated with a bonding solution and allowed to dry at 65° C. to its final form. The bonding solution used was SPENLITE L89 polyurethane coating.

Example 2

Using the equipment set-up and procedure described above to form the initial fiber, and a procedure similar to that described in Example 1 to form the final floss, the following self-bulking flosses were formed:

| Sample No.: | 1 | 2 | 3 | 4 |
| --- | --- | --- | --- | --- |
| Components | Nylon 6 (2.7 RV) Polyester (0.64 MFI) | Nylon 6 (4.0 RV) Polyester (0.64 MFI) | Nylon 6 (2.7 RV) Polyester (0.64 MFI) | Polyester 0.64 MFI Polypro. 12 MFI |
| Ratio | 70/30 | 70/30 | 50/50 | 50/50 |
| Cross-section | side-by-side | side-by-side | hollow pie | hollow pie |
| Drawdown Ratio | 3.28 | 3.5 | 2.2 | 2.2 |
| # of filaments | 144 | 144 | 144 | 144 |
| Total denier | 533 | 863 | 1178 | 982 |
| Color | blue (in nylon) | beige (in nylon) | blue (in nylon) | none added |
| Tensile strength (g/denier) | 3.8 | 3.3 | 1.9 | 1.5 |
| Break strength (kg.) | 2.04 | 2.85 | 2.25 | 1.49 |
| Comments | bulked well; changed color | bulked very well; changed color | did not bulk as well | bulked very well |

Example 3

Using the equipment set-up and procedure described above to form the initial fiber, and a procedure similar to that described in Example 1 to form the final floss, the following tension-induced bulking flosses were formed:

| Sample No.: | 1 | 2 | 3 | 4 |
| --- | --- | --- | --- | --- |
| Components | Nylon 6 (2.7 RV) Polyester (0.64 MFI) | Polyester (0.64 MFI) Polypro. (12 MFI) | Nylon 6 (2.7 RV) Polypro. (12 MFI) | Nylon 6 4.0 RV Polyester 0.64 MFI |
| Ratio | 70/30 | 50/50 | 50/50 | 70/30 |
| Cross-section | side-by-side | hollow pie 16 segmts | hollow pie 16 segmts | side-by-side |
| Drawdown Ratio | 1 | 1 | 1 | 1 |
| # of filaments | 144 | 144 | 144 | 144 |
| Total denier | 2758 | 2205 | 1966 | 2355 |

-continued

| Sample No.: | 1 | 2 | 3 | 4 |
|---|---|---|---|---|
| Color/flavor | blue (in nylon) | green & mint (in polypro) | green & mint (in polypro) | blue (in nylon) |
| Tensile strength (g/denier) | 1.2 | 0.7 | 1.1 | 0.8 |
| Break strength (kg.) | 3.32 | 1.54 | 2.24 | 1.82 |
| Comments | bulked well; changed color | bulked well; changed color; released flavor upon bulking | bulked well; changed color; released flavor upon bulking | bulked well; changed color |

Example 4

Using the same equipment set-up and procedures described above, the following specialty bicomponent flosses were formed:

| Sample No.: | 1 | 2 |
|---|---|---|
| Components | TPE (PEBAX 2533) Nylon (4.0 RV) | TPE (HYTREL 3078) Nylon (4.0 RV) |
| Ratio | 30/70 | 30/70 |
| Cross-section | Sheath/core | Sheath/core |
| Drawdown ratio | 3.5 | 3.4 |
| # of filaments | 144 | 144 |
| Total Denier | 580 | 732 |
| Tensile strength (g/denier) | 5.0 | 4.1 |
| Break strength (kg.) | 2.92 | 3.02 |
| Color | none | none |
| Comments | Fiber needs no bonding or twisting - can be used directly as floss by passing through heated draw rolls; non-bulking | non-bulking |

Example 5

Figure 5:
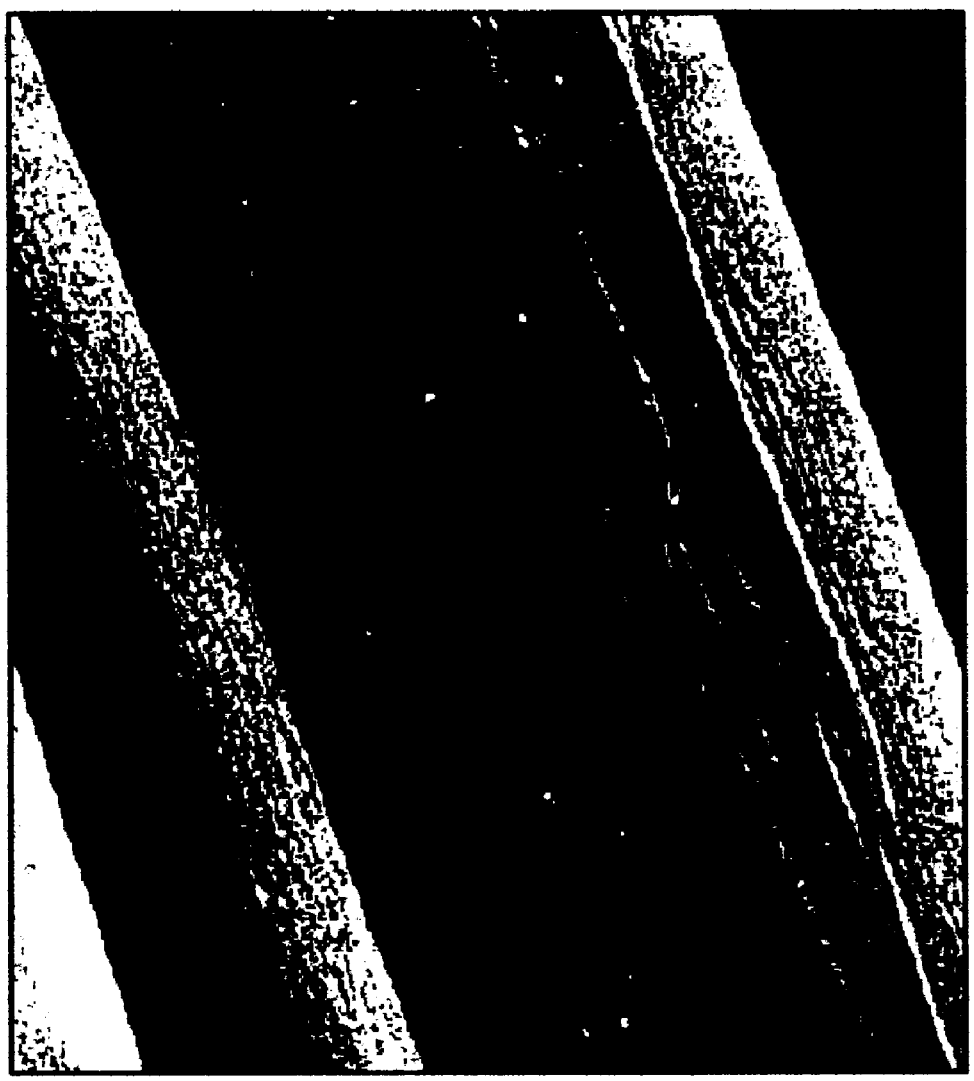
FIG. 5 is an electronmicrograph of a filament containing kaolin particles in its sheath component.

Using the same equipment set-up and procedures described above, the following specialty bicomponent floss was formed:

| Sample No.: | 1 |
|---|---|
| Components | Nylon (4.0 RV) Nylon (4.0 RV) |
| Ratio | 30/70 |
| Cross-section | Sheath/core |
| Drawdown ratio | 3.0 |
| # of filaments | 144 |
| Total Denier | 622 |
| Tensile strength (g/denier) | 3.4 |
| Break strength (kg.) | 2.11 |
| Additive | 2% kaolin in sheath |
| Comments | kaolin particles on surface observable in electron micrograph (see FIG. 5) |

Other embodiments are within the claims.

For example, while bicomponent filaments have been described above in the Detailed Description, the filaments could contain any desired number of components, and in this case would be manufactured by extrusion through a suitable multicomponent die using the appropriate number of extruders.

We claim:

1. A dental floss comprising a plurality of multicomponent coextruded filaments, wherein at least one of the components of said multicomponent filament is a thermoplastic elastomer.

2. The dental floss of claim 1 wherein each said filament consists of two components.

3. The dental floss of claim 1, wherein said thermoplastic elastomer is a polyether block amide.

4. The dental floss of claim 1 wherein the longitudinal axes of said filaments are arranged substantially parallel to each other to form a fiber.

5. The dental floss of claim 4 wherein said fiber is twisted.

6. The dental floss of claim 1 wherein each filament comprises a first component having a predetermined viscoelasticity and a second component having a different viscoelasticity.

7. The dental floss of claim 1 wherein each filament comprises a first component having a predetermined crystalline structure and a second component having a different crystalline structure.

8. The dental floss of claim 1 wherein said components of each said multicomponent filament have different radial cross-sectional geometries.

9. The dental floss of claim 1 wherein at least a portion of said filaments are pretensioned during manufacture and, when tension is released, the filaments relax causing the floss to bulk.

10. The dental floss of claim 1 wherein said multicomponent filaments include two or more components selected to have different relaxation rates.

11. The dental floss of claim 1 wherein said multicomponent filaments are selected to have a degree of interfacial adhesion that allows the filaments to bulk upon application of tension to the filaments.

12. The dental floss of claim 1 wherein said floss is adapted to be bulked by a user of the floss immediately prior to or during use by application of tension to the floss.

13. The dental floss of claim 1 wherein said filaments include a first component selected to provide strength to the floss, and a second component selected to provide a surface having predetermined physical characteristics.

14. The dental floss of claim 13 wherein said first component forms an inner core and said second component forms a sheath surrounding said core.

15. The dental floss of claim 13 wherein said first component comprises a polymer selected from the group consisting of nylon, polyester and polypropylene.

16. The dental floss of claim 13 wherein said second component comprises a melt extrudable polymer selected from the group consisting of thermoplastic elastomers, ethylene vinyl acetate, ethylene propylene copolymers, fluoropolymers, lubricating polymers, and lubricious polymer alloys.

17. The dental floss of claim 16 wherein said second component comprises a thermoplastic elastomer.

18. The dental floss of claim 13 wherein said second component comprises a blend of a melt extrudable polymer and a silicone oil.

19. The dental floss of claim 13 wherein said second component comprises a blend of a melt extrudable polymer and a particulate filler selected from the group consisting of kaolin, calcium carbonates silica, and polytetrafluoroethylene.

20. The dental floss of claim 19 wherein an additive is adsorbed or absorbed onto a surface of said particulate filler.

21. The dental floss of claim 1 or 13 wherein one or more of the components of the multicomponent filaments includes an additive.

22. The dental floss of claim 21 wherein the additive is selected from the group consisting of colors, fragrances, flavors, active ingredients, and agents which modify the interfacial adhesion between the components of the filaments.

23. The dental floss of claim 21 wherein the additive is incorporated in a manner to allow it to be released from the floss during use.

24. The dental floss of claim 21 wherein one or more of the components of the multicomponent filaments are water-soluble, to allow the additive to leach from the floss during use.

25. The dental floss of claim 21 wherein the components of the multicomponent filaments are selected to render the dental floss capable of bulking.

26. The dental floss of claim 25 wherein the additive is a color and is incorporated in a manner to enable the dental floss to change color upon bulking.

27. The dental floss of claim 25 wherein the additive is incorporated in a manner to allow it to be released from the floss upon bulking.

28. A dental floss comprising a plurality of filaments having a multilobal radial cross-section.

29. The dental floss of claim 28 wherein said filaments have from 3 to 8 lobes.

30. The dental floss of claim 28 wherein at least a portion of the filaments individually comprise two or more coextruded components.

31. The dental floss of claim 30 wherein said two or more components are selected to render the dental floss capable of bulking.

32. The dental floss of claim 30 wherein said filaments have a sheath/core radial cross-section.

33. The dental floss of claim 30 wherein said filaments have a tipped radial cross-section.

* * * * *